United States Patent
Veale et al.

(10) Patent No.: US 7,067,323 B2
(45) Date of Patent: Jun. 27, 2006

(54) SYSTEM AND METHOD FOR AUTOMATED HEADSPACE ANALYSIS

(75) Inventors: James R. Veale, Charlottesville, VA (US); William R. Anderson, Charlottesville, VA (US); Warren M. Griffith, Charlottesville, VA (US); Glenn E. Edwards, Palo Alto, CA (US); George R. Howard, Kennett Square, PA (US)

(73) Assignee: Lighthouse Instruments, LLC, Charlottesville, VA (US)

( * ) Notice: Subject to any disclaimer, the term of this patent is extended or adjusted under 35 U.S.C. 154(b) by 74 days.

(21) Appl. No.: 10/684,412

(22) Filed: Oct. 15, 2003

(65) Prior Publication Data
US 2005/0084974 A1    Apr. 21, 2005

(51) Int. Cl.
*G01N 33/15* (2006.01)
*G01N 33/18* (2006.01)
*G01N 21/62* (2006.01)

(52) U.S. Cl. ............... 436/136; 73/866.5; 250/343; 422/62; 422/63; 422/64; 422/65; 422/67; 436/43; 436/47; 436/127; 436/133; 436/134; 436/171

(58) Field of Classification Search ........... 73/866.5; 250/223 B, 343; 422/62–65, 67; 436/43, 436/47, 127, 133–134, 136, 171
See application file for complete search history.

(56) References Cited

U.S. PATENT DOCUMENTS

| | | | | |
|---|---|---|---|---|
| 4,376,951 A | * | 3/1983 | Miyazawa | 348/127 |
| 4,578,762 A | | 3/1986 | Wong | |
| 5,060,505 A | | 10/1991 | Tury et al. | |
| 5,293,210 A | * | 3/1994 | Berndt | 356/39 |
| 5,310,658 A | * | 5/1994 | Berndt | 435/34 |
| 5,315,108 A | * | 5/1994 | Gross | 250/223 B |
| 5,334,536 A | | 8/1994 | Nonnenmacher | |
| 5,371,016 A | * | 12/1994 | Berndt | 435/288.7 |
| 5,387,971 A | | 2/1995 | Koashi et al. | |
| 5,397,709 A | * | 3/1995 | Berndt | 436/34 |
| 5,451,787 A | | 9/1995 | Taylor | |
| 5,468,962 A | | 11/1995 | Ohishi et al. | |
| 5,473,161 A | * | 12/1995 | Nix et al. | 250/343 |
| 5,474,665 A | | 12/1995 | Friese et al. | |
| 5,485,527 A | | 1/1996 | Bacus et al. | |
| 5,572,031 A | | 11/1996 | Cooper et al. | |

(Continued)

FOREIGN PATENT DOCUMENTS

JP    9-127001    *   5/1997

(Continued)

OTHER PUBLICATIONS

Bailey, G. F. et al, Journal of Parenteral Drug Association 1980, 34, 127-133.*

(Continued)

*Primary Examiner*—Arlen Soderquist
(74) *Attorney, Agent, or Firm*—Greenblum & Bernstein, P.L.C.

(57) ABSTRACT

A system and method for nondestructive automated headspace analysis. The system includes a container conveyor that conveys a plurality of generally optically transparent sealed test containers through a pre-inspection region, an inspection region and a post-inspection region of the container conveyor, and that conveys at least one sealed reference container, through the inspection region. Also included is a zone including a laser emitter and a sensor located in the inspection region and arranged such that the laser source emits a laser beam such that it intersects with a container movement path. The conveyor alternatingly conveys test containers and reference containers through the zone.

38 Claims, 5 Drawing Sheets

U.S. PATENT DOCUMENTS

| | | |
|---|---|---|
| 5,637,872 A | 6/1997 | Tulip |
| 5,677,534 A | 10/1997 | Araya |
| 5,703,365 A | 12/1997 | Ishihara et al. |
| 5,755,335 A * | 5/1998 | Michelotti et al. .......... 209/528 |
| 5,821,537 A | 10/1998 | Ishihara et al. |
| 5,886,247 A | 3/1999 | Rabbett |
| 5,892,577 A | 4/1999 | Gordon |
| 5,930,000 A | 7/1999 | Brand |
| 6,001,499 A | 12/1999 | Grot et al. |
| 6,006,585 A | 12/1999 | Forster |
| 6,055,876 A | 5/2000 | Kato |
| 6,121,627 A | 9/2000 | Tulip |
| 6,157,033 A | 12/2000 | Chudnovsky |
| 6,267,927 B1 | 7/2001 | Longedo et al. |
| 6,274,879 B1 | 8/2001 | Best-Timman |
| 6,359,278 B1 | 3/2002 | Graham |
| 6,483,589 B1 | 11/2002 | Suzuki et al. |
| 6,525,813 B1 | 2/2003 | Yokota |
| 6,639,678 B1 * | 10/2003 | Veale ........................ 356/437 |
| 6,709,857 B1 * | 3/2004 | Bachur, Jr. ............... 435/288.7 |

FOREIGN PATENT DOCUMENTS

| | | | |
|---|---|---|---|
| RU | 2100804 | * | 12/1997 |
| WO | 96/02835 | * | 2/1996 |

OTHER PUBLICATIONS

Jungst, R. G. et al, SPIE 1981, 288, 245-252.*

Powell, L. P. et al, Analytical Chemistry 1988, 58, 2350-2352.*

Dausch, M. et al, Technisches Messen 1996, 63, 288-290.*

* cited by examiner

SYSTEM AND METHOD FOR AUTOMATED HEADSPACE ANALYSIS

This invention was made with Government support, under Grant No. R44FD-01570-03-2, awarded by the U.S. Food and Drug Administration. The Government has certain rights in the invention.

BACKGROUND OF THE INVENTION

1. Field of the Invention

The present invention is related to sensing devices using laser spectroscopy, and more particularly, is related to headspace sensing and analysis of sealed optically-transparent containers that are moved along a conveyor.

2. Background and Material Information

Tunable diode laser absorption spectroscopy (TDLAS) is a high sensitivity measurement method well-suited to monitoring gases in small volume containers for manufacturing process and quality control applications.

For automated package inspection applications where gas concentrations and/or pressures need to be measured in individual product containers at high speed, a spectroscopic system must be designed to move individual samples through a measurement region, and the sensing system is designed to automatically self-calibrate and perform self diagnostics.

Most TDLAS systems are configured for analyzing gas samples using stationary sample cells and reference cells. A typical system is described by COOPER et al. (U.S. Pat. No. 5,572,031) where a single laser beam is split into two laser beams using a beam splitter. In such a system, one optical path passes through the sample cell (containing e.g., a gas to be measured, tested and/or checked) and the second passing through a reference cell. The light directed along the reference and sample paths are then collected by separate detectors.

The art is replete with TDLAS systems similar to COOPER that employ stationary dual detectors and stationary sample and reference cells. In such systems, the laser beam is split and passed separately through a sample cell and reference cell. This arrangement has many shortcomings and undesirable effects. First, the use of beam splitting optics in TDLAS systems leads to optical interference fringes that reduce measurement sensitivity, especially when testing for weakly-absorbing samples, such as oxygen. Second, the use of two detectors, one detector to calibrate and a second detector to sample leads to uncertainties about the validity of the system calibration in the sample path. Third, the use of fixed sample and reference cells necessitates that the sample gas be introduced to the sample cell for measurement. This last point is particularly undesirable if the sample is contained in a finished product ready for shipment as opposed to a process stream that can be sampled.

Many new and existing commercial products, e.g., pharmaceutical, food, beverage and consumer electronics, have ingredients that are sensitive to atmospheric gases. Prolonged exposure to elevated levels of these gases (e.g., oxygen and moisture) degrades product quality and potency. When processing gas-sensitive formulations, ambient levels of reactive gases are reduced with inert gas purges or packages are sealed under vacuum. Thus, a fast, sensitive, and nondestructive method and apparatus for continuous monitoring of gas concentrations and pressures in sealed product containers as they move along a conveyor is desired.

SUMMARY OF THE INVENTION

Accordingly, it is a feature of the invention to provide "real time" analysis of moving sample vials, as well as real time calibrating and recalibrating.

Another feature of the invention provides for the easy and reliable detection of oxygen, moisture and other gas concentrations and/or pressures, in containers that hold a small volume of product, such as during the production of pharmaceutical, food, beverage and consumer electronics production. For example, the present invention may analyze the contents of sample containers as small as 1 cc.

The invention also provides for the analysis of samples at "real time" production speeds (i.e., samples may be analyzed at speeds which keep up with the speed of the rest of the production line), provides for the measurement of trace substance (e.g., gas) quantities, and further provides for the nondestructive analysis of concentration and/or pressure levels thereof within sealed containers.

Additionally, since the present invention provides for the automatic testing of large quantities of samples for the presence of atmospheric gases, moisture and/or vacuum levels at high speed (e.g., speeds up to and in excess of 300 containers per minute) over extended periods of time, the present invention also properly positions a sample in the sensing zone for a sufficient time to measure the absorption signal to determine gas concentration and/or pressure, optionally by slowing down a portion of the conveyor in the sensing zone while not slowing down overall throughput of the present invention.

The present invention is further capable of self-calibrating by measuring known concentrations and/or pressure by using reference vials between sample measurements.

The present invention provides a system for nondestructive automated headspace analysis including a container conveyor configured to convey, along a movement path, a plurality of generally optically transparent sealed test containers each configured to contain a gas to be measured, through a pre-inspection region, an inspection region and a post-inspection region of the container conveyor, and convey, along the movement path, at least one sealed reference container through the inspection region, the at least one sealed reference container containing a reference gas. Also provided is a sensor located in the inspection region and including a laser source configured to emit a laser beam for absorption in the gas to be measured and the reference gas, the laser source further configured to emit the laser beam such that the laser beam intersects with the movement path, a beam detector configured to detect the laser beam, and a zone configured to accept the plurality of test containers and the at least one reference container conveyed by the container conveyor, the zone located between the detector and the laser source. The container conveyor is further configured to alternatingly convey at least one sealed test container of the plurality of sealed test containers and the at least one sealed reference container through the zone.

The at least one sealed reference container may be a plurality of sealed reference containers.

Also, the plurality of sealed reference containers may include a first plurality of sealed reference containers corresponding to a first range of reference gas characteristics, and a second plurality of sealed reference containers corresponding to a second range of reference gas characteristics, and the laser source may include a first laser source configured to emit a first laser beam that intersects a movement path of the first plurality of sealed reference containers, and a second laser source configured to emit a second laser beam that intersects a movement path of the second plurality of sealed reference containers. The detector may include a first detector configured to detect the first laser beam, and a second detector configured to detect the second laser beam.

The invention may also include a processor configured to check, using the first and second pluralities of sealed reference containers, the calibration of the detector respectively over the first range of reference gas characteristics, and over the second range of reference gas characteristics. Also, the first and second characteristics may be pressure and concentration. Further, wherein the reference gas may be a respective first and second different reference gas.

Moreover, each sealed reference container of the plurality of reference containers may contain a reference gas within a range of reference gas characteristics. The invention may also include a processor configured to check the calibration of the detector over the range using the plurality of reference containers.

The container conveyor may include a rotatable starwheel located at the inspection region, the starwheel configured to accept the plurality of sealed test containers from the pre-inspection region, convey the at least one sealed test container and the at least one sealed reference container through the zone, and convey the plurality of sealed test containers to the post inspection region, the plurality of sealed reference container may be affixed to the starwheel, and the zone may be located at a portion of the starwheel.

The starwheel may be configured to convey the at least one sealed test container through the zone at a slower rate than when the starwheel is not passing the at least one sealed test container through the zone. Also, the container conveyor may convey the at least one sealed test container through the zone at a slower rate than when the container conveyor is not passing the at least one sealed test container through the zone.

Also, a purging system may be provided to purge ambient surroundings of the zone of the gas to be measured.

The starwheel may be configured such that a single sealed test container of the plurality of sealed test containers is held between a pair of sealed reference containers of the plurality of sealed reference containers. Also, the starwheel may be configured such that a single sealed reference container of the pair of sealed reference containers is held between a pair of sealed test containers of the plurality of sealed test containers.

Also, the container conveyor may include a linear feeder located at the inspection region, the linear feeder configured to accept the plurality of sealed test containers from the pre-inspection region, convey the at least one sealed test container and the at least one sealed reference container through the zone, and convey the plurality of sealed test containers to the post inspection region, and the plurality of sealed reference container may be affixed to the linear feeder, and the zone may be located at a portion of the linear feeder.

The linear feeder may be configured to convey the at least one sealed test container through the zone at a slower rate than when the linear feeder is not passing the at least one sealed test container through the zone. Also, the laser source and the beam detector may be configured to move in a direction substantially parallel to the movement path of the at least one sealed test container when the at least one sealed test container is conveyed through the zone.

The method for automated nondestructive headspace analysis includes conveying, along a movement path, a plurality of generally optically transparent sealed test containers each configured to contain a gas to be measured, through a pre-inspection region, an inspection region and a post-inspection region of a container conveyor, alternatingly conveying, along the movement path, the plurality of test containers, and at least one sealed reference container, through a zone of an inspection region of the container conveyor, transmitting a laser beam in the zone of the inspection region, in a direction that intersects the movement path, and through a single sealed test container of the plurality of test containers, when the single sealed test container is conveyed through the zone, transmitting the laser beam in the zone of the inspection region, in the direction that intersects the movement path, and through a single at least one sealed reference container, when the single sealed reference container is conveyed through the zone, detecting, using a detector, the transmitted laser beam, and conveying, along the movement path, the plurality of test containers through a post-inspection region of a container conveyor.

Further, the plurality of sealed reference containers may include a first plurality of sealed reference containers corresponding to a first range of reference gas characteristics, and a second plurality of sealed reference containers corresponding to a second range of reference gas characteristics. The transmitting the laser beam in the zone of the inspection region, in the direction that intersects the movement path, and through a single at least one sealed reference container, when the single sealed reference container is conveyed through the zone, may include transmitting a first laser beam in the zone of the inspection region, and through a single sealed reference container of the first plurality of reference containers, and transmitting a second laser beam in the zone of the inspection region, and through a single sealed reference container of the second plurality of reference containers.

The method may also include checking, using the first and second pluralities of sealed reference containers, the calibration of the detector respectively over the first range and over the second range. Also, each sealed reference container of the plurality of reference containers may contain a reference gas within a range of reference gas characteristics.

The method may additionally include checking the calibration of the detector over the range, using the plurality of sealed reference containers.

In the method, the alternately conveying may include accepting, using a starwheel, the plurality of sealed test containers from the pre-inspection region, conveying, using the starwheel, the at least one sealed test container and the at least one sealed reference container through the zone, and conveying the plurality of sealed test containers to the post inspection region. Also, the plurality of sealed reference containers may be affixed to the starwheel, and the zone may be located at a portion of the starwheel.

Also, the conveying, using the starwheel, the at least one sealed test container and the at least one sealed reference container through the zone may include conveying the at least one sealed test container through the zone at a slower rate than when the starwheel is not passing the at least one sealed test container through the zone.

Further, the alternately conveying may include conveying the at least one sealed test container through the zone at a slower rate than when the at least one sealed test container is not conveyed through the zone.

The method may also include purging ambient surroundings of the zone of the gas to be measured.

The method may further include arranging, on the starwheel, a single sealed test container of the plurality of sealed test containers between a pair of sealed reference containers of the plurality of sealed reference containers. Also, the method according to claim 30, further comprising arranging, on the starwheel, a single sealed reference container of the pair of sealed reference containers between a pair of sealed test containers of the plurality of sealed test containers.

The alternately conveying may include accepting, using a linear conveyor, the plurality of sealed test containers from the pre-inspection region, conveying, using the linear conveyor, the at least one sealed test container and the at least one sealed reference container through the zone, and conveying the plurality of sealed test containers to the post inspection region, the plurality of sealed reference containers may be affixed to the linear conveyor, and the zone may be located at a portion of the linear conveyor.

Additionally, the conveying, using the linear conveyor, the at least one sealed test container and the at least one sealed reference container through the zone may include conveying the at least one sealed test container through the zone at a slower rate than when the linear conveyor is not passing the at least one sealed test container through the zone.

The method may yet include moving the laser beam and the beam detector in a direction substantially parallel to the movement path of the at least one sealed test container when the at least one sealed test container is conveyed through the zone.

The alternately conveying may include accepting the plurality of sealed test containers from the pre-inspection region, successively conveying the plurality of test containers and a plurality of the reference containers through the zone, such that the laser beam successively passes through the plurality of test containers and the plurality of reference containers, and conveying the plurality of sealed test containers to the post inspection region.

Further, the alternately conveying may include accepting the plurality of sealed test containers from the pre-inspection region, successively conveying the plurality of test containers and a single one of the at least one reference container through the zone, such that the laser beam successively passes through the plurality of test containers and the single reference container, and conveying the plurality of sealed test containers to the post inspection region.

Still yet, the alternately conveying may include accepting the plurality of sealed test containers from the pre-inspection region, successively conveying a single one of the plurality of test containers and a plurality of the reference containers through the zone, such that the laser beam successively passes through the single test container and the plurality of reference containers, and conveying the plurality of sealed test containers to the post inspection region.

Further, the alternately conveying may include accepting the plurality of sealed test containers from the pre-inspection region, successively conveying a single one of the plurality of test containers and a single one of the plurality of the reference containers through the zone, such that the laser beam successively passes through the single test container and the single reference container, and conveying the plurality of sealed test containers to the post inspection region.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of non-limiting examples of preferred embodiments of the present invention, in which like numerals represent like elements throughout the several views of the drawings, and wherein.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

It is an overall concept of the invention to provide for the accurate inspection of sample vials by moving these sample vials, together with at least one reference vial, along a path through an inspection zone such that the same laser beam passes through both a sample vial and the reference vial onto a beam detector, as the sample vials and reference vials pass through the inspection zone. For example, a laser source can be positioned in a zone of a product line, in order to emit a beam through sample vials and reference vials, as the sample vials and reference vials pass through the zone in their path of movement. For example, one or more sample vials can be analyzed, followed by analyzing one or more reference vials, followed by analyzing one or more sample vials, etc.

Figure 1:
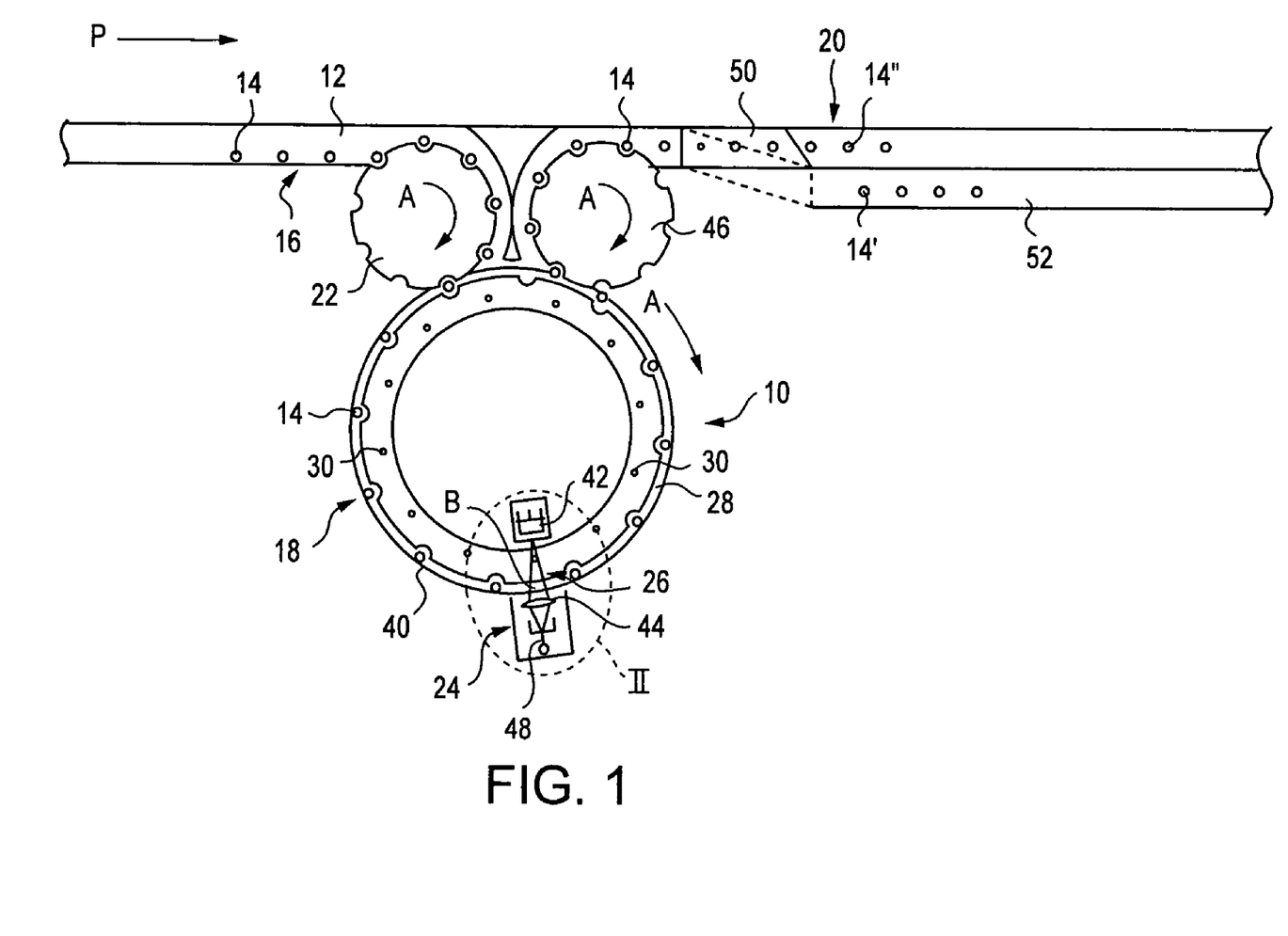
FIG. 1 is a schematic plan view of system for automated headspace gas analysis according to a first embodiment of the invention.

Referring to the drawings wherein like numerals represent like elements, FIG. 1 shows a schematic view of a system for automated headspace analysis 10 for use in e.g., a production line. The system includes a conveyor 12 that conveys a plurality of sealed generally optically transparent sample containers (e.g. vials) 14, which may be made of glass, plastic, and the like, from one section of the production line to another. It is understood that in the present specification, the term "generally optically transparent" means that a laser beam B can pass through the containers 14, 30. Thus, the containers can be completely or substantially transparent, and may be colored and/or translucent. These sample vials 14 may contain, e.g., pharmaceutical, food, beverage and consumer electronics products therein, which may be in solid, liquid or powderous form (e.g., lyophilized form), and which are stored therein under controlled conditions (e.g., in a vacuum, with nitrogen backfill, etc.). Also the sample vials 14 may be completely gaseous, i.e., the headspace comprises the entire vial contents.

The conveyor 12 conveys the sample vials 14 through a pre-inspection region 16, an inspection region 18 and a post-inspection region 20 along a path P. A pre-inspection starwheel 22 moves the sample vials 14 from the a pre-inspection region 16 to the inspection region 18 by rotating in a clockwise direction A (as viewed in FIG. 1). When starwheels 22, 28, 46 are conveying the sample vials, it is understood that the path of movement P of the sample vials is the same as the movement direction of movement A of the starwheels. It is readily appreciable by those skilled in the art that the present invention may use other ways to convey the sample vials 14 from the a pre-inspection region 16 to the inspection region 18. For example, and without limitation, sample vials may be conveyed by a mechanical arm, conveyor belts, etc.

Figure 2:
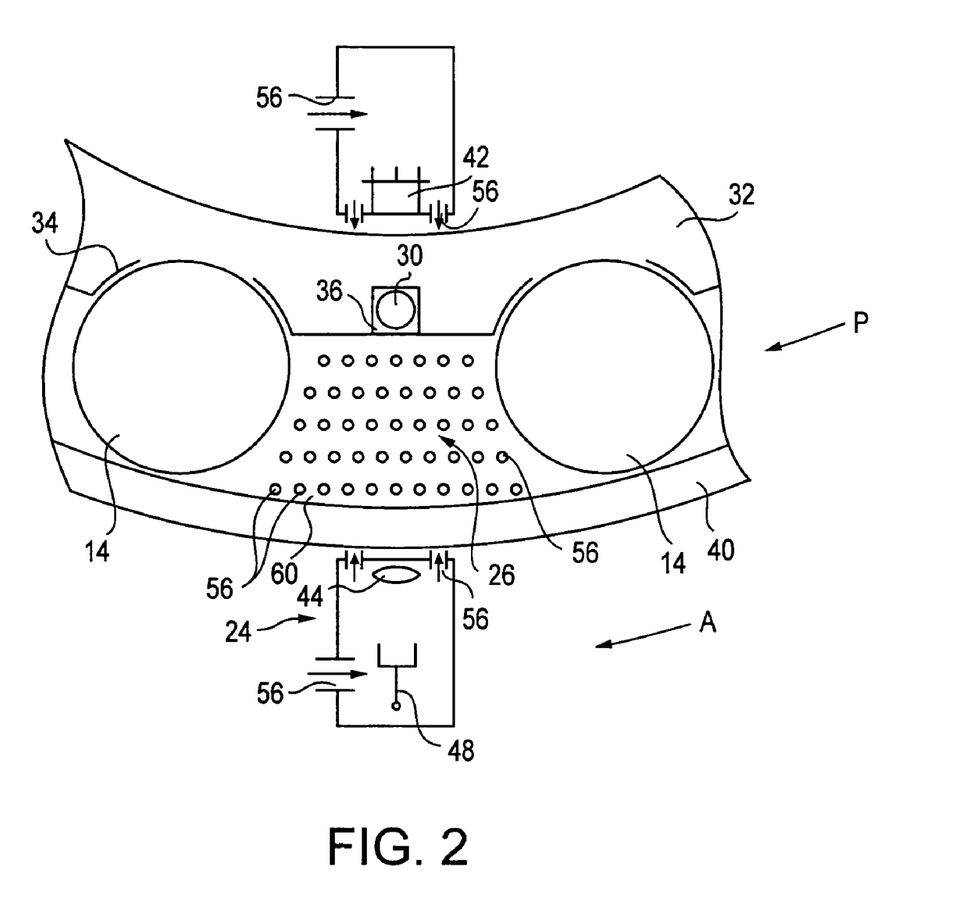
FIG. 2 is an enlarged schematic view of region II of FIG. 1.

As best shown in FIG. 2, which is an enlarged schematic view of region II of FIG. 1, once the sample vials 14 are conveyed to the inspection region 18, they are then conveyed to a sensing zone 26, by clockwise-rotating inspection starwheel 28 (as viewed in FIG. 1). The inspection starwheel 28 also includes at least one reference vial 30 affixed thereto, which stays on the starwheel (i.e., it does not move from beyond the inspection region, but may be removed for replacement). The starwheel 28 has a vial accommodation portion 32, which accommodates the sample vials 14 in respective sample vial housings 34 as they are conveyed through the inspection region 18. The inspection starwheel 28 also accommodates the reference vials 30 in reference vial housings 36. The vial accommodation portion 32 is rotatable in the direction A, while retainer portion 40 of the inspection starwheel 28 do not rotate. Once in the sensing zone 26, the headspace substance (e.g. gas) is detected by a sensing system 24. In one embodiment, a TDLAS system of the kind described in U.S. patent application Ser. No. 09/615,739 the contents of which are expressly incorporated by reference herein in its entirety, may be used because of this system's ability to reduce the quantity of optical interference fringes. As best shown in FIG. 2, such a TDLAS system includes a laser emitter 42 located on one side of the direction of movement of the sample vials 14 and reference vial 30, which emits an uncollimated (i.e. diverging) laser beam B (shown in FIGS. 1 and 3A) through the sensing zone 26, across the path of movement P of the sample vials, through a collection lens 44, which focuses the laser beam onto a laser detector 48. The laser emitter 42 may be adjusted to emit the beam B at a frequency corresponding to the absorption frequency or an atom or molecule of the substance to be measured (e.g., a gas such as oxygen or moisture vapor).

While the figures show a TDLAS system used in the present invention, it is readily appreciable by those skilled in the art that the present invention may use other types of sensing in alternative embodiments, e.g., by emitting a collimated laser beam onto a sensor without using the collection lens.

Figure 3A:
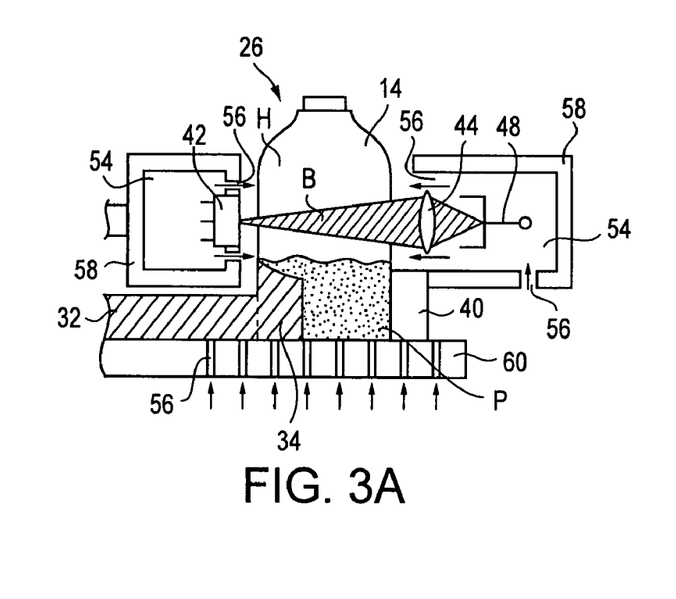
FIG. 3A is a schematic side view showing a test container in the inspection zone of the system of the first embodiment of the invention.
Figure 3B:
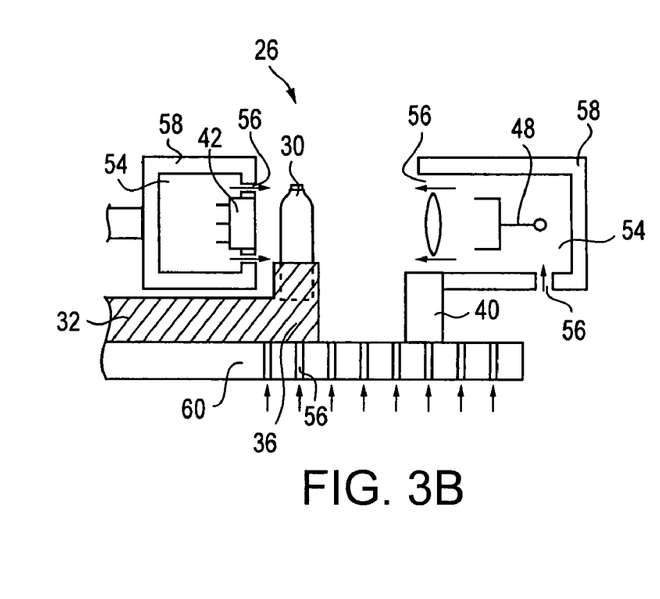
FIG. 3B is a schematic side view showing a reference container in the inspection zone of the system of the first embodiment of the invention.

The sensing system 24 is connected to a computer processor (not shown), which determines whether the system is properly calibrated (or otherwise functioning properly, e.g., whether the emitter 42 and/or detector 48 is on) and whether the sample vials meet a predetermined quality level (e.g., in the latter, based on the detected characteristic of the gas in the reference vial 30 when compared to a properly calibrated reference vial(s) 30). When a sample vial 14 or reference vial 30 is present in the sensing zone 26, as shown in FIGS. 3A and 3B respectively, the beam also passes through the walls of the vials. As shown in FIG. 3A, the beam passes through the walls of the vials at a headspace region H (i.e., the part of the vial not containing the product p) of the sample vial 14 so that the detector can detect the presence or other quantity or quality of the gas to be measured in the headspace region H.

As shown in FIG. 3B, the reference vials 30 do not contain the product p. Rather, in the embodiment shown in the figures, the reference vials contain a reference gas similar to what the detector is set to detect, to provide for calibration of the detector 48. For example, when the processor is configured to check for the presence of oxygen in the headspace H of the sample vials 14, a predetermined known concentration of oxygen is provided in each reference vial (which may or may not be different from each other). Thus, when the reference vial 30 containing this known concentration of oxygen is detected in the sensing zone 26 by the detector 42, a properly calibrated sensing system 24 will detect this exact concentration of oxygen. If the sensing system 24 detects a concentration of oxygen different from the predetermined amount in the reference vial 30, the processor then determines that the sensing system is out of calibration, and may reject (or otherwise identify) sample vials 14 that were analyzed by the sensing system after it was determined that the sensing system was properly calibrated, but sample vials 14 analyzed before the previous time the reference vial 30 was checked (i.e., when the reference vial 30 returned a signal indicated that the sensing system 24 was properly calibrated) need not be discarded. Also, all of the sample vials 14 in the inspection starwheel may be rejected once it has been determined by the processor that the sensing system 24 is improperly calibrated.

As a non-limiting example, the sensing system may be calibrated as follows: After the processor has determined that the sensing system 24 is improperly calibrated (i.e., the sensing system returns a signal value different from the known characteristic of the reference vial 30), the processor instructs the invention 10 to empty the inspection starwheel 28 of sample vials 14, and to no longer accept any sample vials during the calibration process. Once empty, the sensing system 24 may then recalibrate itself in accordance with (i.e., such that the signal value returned to the sensing system corresponds to) the reference characteristic of each respective reference vial 30, by rotating the starwheel 28 such that each reference vial is sensed by the sensing system 24, thereby recalibrating the sensing system. Once the sensing system has been recalibrated, the starwheel may again accept and analyze sample vials 14. Alternatively, the sensing system 24 may be manually calibrated using a similar method.

In the preferred embodiment, there is a reference vial 30 between each sample vial (i.e., there is a single reference vial 30 alternatingly placed after a single sample vial 14), as shown in the Figures, but in alternative embodiments only a single reference vial 30 may be provided as a sensor check vial in the inspection region 18 and conveyed through the sensing zone 26, to provide for a qualitative check of the sensor, e.g., whether the emitter 42 and/or detector 48 is on. Still alternatively, in the inspection region 18, there may be a plurality of sample vials 14 located between reference vials 30 and/or there may be a plurality of reference vials 30 between sample vials 13. In this regard, it is understood that, throughout the specification, the term "alternately conveying" at least one sample vial 14 and at least one reference vial 30 through the sensing zone 26 means that, in addition to conveying a single reference vial 30 after a single sample vial 14 in cycles through the sensing zone, also means that in the present invention: a plurality of reference vials can be conveyed after a single sample vial in cycles through the sensing zone; a single reference vial can be conveyed after a plurality of sample vials in cycles through the sensing zone; and/or a plurality of reference vials can be conveyed after a plurality of sample vials in cycles through the sensing zone. It is also understood by those skilled in the art that rather than conveying one or more reference vials 30 after one or more sample vials 14, one or more reference vials can be conveyed before one or more sample vials. Without wishing to be bound by theory, it is preferred that the invention 10 be configured so as to reject as few sample vials as possible once it has been determined that the sensing system is out of calibration.

In embodiments where there is a plurality of reference vials 30 in the inspection region 18, it is preferred that characteristics of the reference gas in the reference vials 30 vary (i.e. within a characteristic range) so that the processor could check the sensing system 24 over a calibration range, rather than just a single calibration. In the preferred embodiment, to ensure proper linearity of calibration accuracy, at least three reference vials 30 are preferably used, the reference gas in each having a different characteristic. In the above example, when testing for oxygen, first reference vial 30 may contain 0% oxygen, a second reference vial may contain 10% oxygen, and a third reference vial may contain 20% oxygen, thereby allowing the processor to check for sensing system 24 calibration over a range of 0–20%.

Further, the present invention is not limited to checking concentrations of a single reference gas. For example, in addition or alternative to checking the concentrations of a reference gas, the reference vials may be filled with a plurality of reference gases that vary over a range of pressures, and the processor may be configured to check for one or both of reference gas concentration and reference gas pressure. Also, the concentrations and/or pressures of two or more different references gases may be analyzed by the present invention. Examples of such reference gases may be $CO_2$, oxygen, water vapor, etc.

Figure 5:
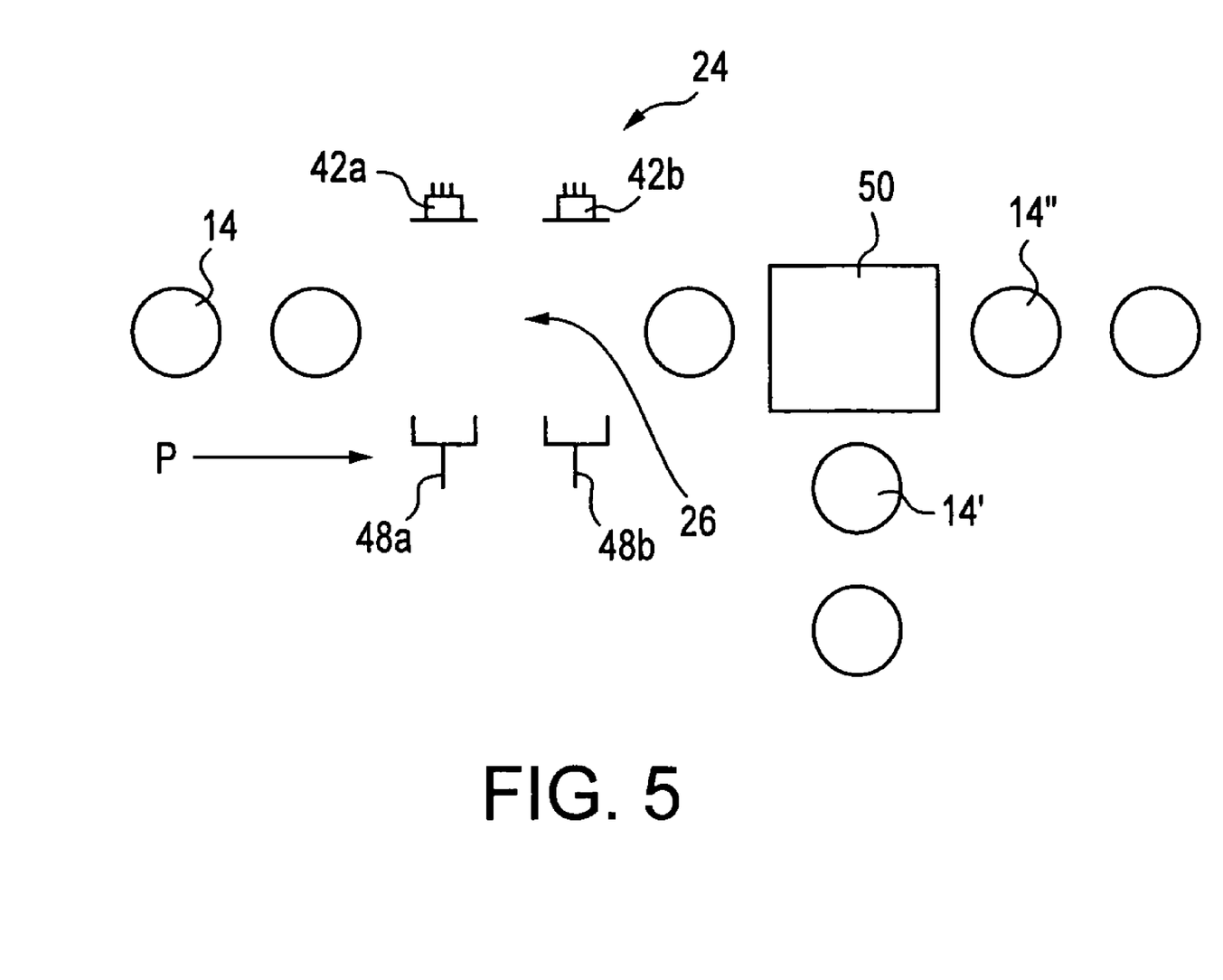
FIG. 5 is a schematic plan view of a sensing system according to a further embodiment of the invention.

When analyzing more than one reference gas concentration, more than one reference gas pressure, or analyzing reference gas concentrations together with reference gas pressures, it is advantageous for the sensing zone 26 of the sensing system 24 to utilize more than one laser emitter 42 and laser detector 48, e.g., a different laser emitter 42 and laser detector 42 is used for each gas characteristic to be analyzed. As one non-limiting example, when the present invention is analyzing oxygen pressure and oxygen concentration, two laser emitters 42a, 42b are used to respectively emit a respective beam onto two detectors 48a, 48b, as shown in FIG. 5, wherein detector 48a is configured to detect, e.g., oxygen pressure, and detector 48b is configured to detect, e.g., oxygen concentration. As another non-limiting example, when the present invention is analyzing oxygen pressure, oxygen concentration and carbon dioxide concentration, then three laser emitters and three laser detectors are used. It is also noted that in the present invention, the concentration of one type of gas may be measured along with the pressure of a different type of gas.

In the embodiment shown in FIG. 1, inspection starwheel 28 in the inspection region 18 contains twelve reference vials 30, the quantity of which may vary in alternative embodiments, as described above. Thus, as described above, these twelve reference vials 30 may contain six reference vials having a gas that varies along a range of gas concentration, and six reference vials having a gas that varies along a range of gas pressure. Alternatively, all twelve reference vials 30 may contain a gas that varies along a range of gas pressure or gas concentration. As can be appreciated by those skilled in the art, the number and characteristics of the reference vials 30 may be widely varied depending on the requirements of the product line.

To ensure the accuracy of the sensing system 24, when the inspection starwheel 28 moves a sample vial 14 through the sensing zone 26, wherein a laser beam is passed through the walls of the sample vial, the rate of rotation of the inspection starwheel slows to allow the detector 48 more time to detect the laser beam while it is passing through the walls of the sample vial 14. It may not be necessary to slow the rate of rotation of the inspection starwheel 28 when the reference vial 30 is in the sensing zone 26, since the calibration check using the reference vials may not need as much time as the sample vial check. In fact, the speed of the reference vial 30 may be increased or stay the same as the base speed of the rest of the line. Additionally, when neither reference vials 30 or sample vials 14 are passed through the inspection zone, the speed of the inspection starwheel 28 may be altered to be greater, less than or the same as the speed of the rest of the line.

For example, if the total throughput of the present invention 10 is set to 120 sample vials 14 per minute (based on e.g., 10 cc sample vials 14) to ensure that the present invention keeps up with the online speed of the rest of the production line, this configuration means that one sample vial 14 must be scanned every half second. However, for example, in the present invention, the sample vials 14 are inspected at a rate of one sample vial per $4/10$ of a second, while the reference vials are inspected at a rate of one reference vial per $1/10$ of a second, in a configuration where a single sample vial 14 is consecutively inspected with a single reference vial 30, thereby totaling a half second for both a sample vial 14 and a reference vial 30 and not slowing down the overall throughput of the production line. Thus, the present invention 10 may be implemented in a product line that operates continuously, semi-continuously, intermittently, etc., without affecting the speed of the line. It is noted that those skilled in the art will appreciate that the present invention 10 may be freely adjustable depending on the overall throughput of the production line, the size of the sample vials 14, the user's needs, etc.

As an alternative or in addition to slowing down the sample vials 14 while they are conveyed through the sensing zone 26, the sensing system may 24 be configured to move through the sensing zone in a direction X and substantially parallel to the path of movement P of the sample vials when the sample vials are conveyed through the sensing zone, at a rate slower, faster or the same as the rate of movement of the sample vials, thereby providing the detector 48 with even more time to detect the laser beam while it is passing through the walls of the sample vial 14.

To further ensure the accuracy of the sensing system 24, the sensing system may be equipped with a purging system 54 that purges the sensing zone 26 of the gas to be measured, via a network of passages 56. For example, if the sensing system is configured to detect oxygen in the headspace H, the purging system directs, e.g., nitrogen, through the passages 56 into the sensing zone 26 to purge the area surrounding the vials of moisture and/or oxygen, which would otherwise interfere with the detection of oxygen in the vials 14, 30. Similarly, if the sensing system is configured to detect moisture in the headspace H, the purging system directs dry gas (i.e., gas substantially devoid of moisture), such as dry air or nitrogen, through the passages 56 into the sensing zone 26 to purge the area surrounding the vials of moisture and other unwanted ambient fluid, which would otherwise interfere with the detection of moisture in the vials 14, 30. To prevent leakage of fluid from the purging system, the laser emitter 42 and collection lens 44 and laser detector 48 are enclosed in a housing 58, with the passages 56 therein configured to aspirate fluid from a fluid source (not shown), or configured to direct fluid into the sensing zone 24. Additionally, as shown in FIGS. 2, 3A and 3B, the starwheel includes a non-rotatable table 60 over which the vial accommodation portion 32 rotates, the table also having passages 56 to better direct the fluid into the sensing zone 26.

Once the sample vials 14 have been inspected in the inspection region 18, a post-inspection starwheel 46 conveys the inspected sample vials 14 to the post-inspection area 20, where the conveyor 12 continues to convey the sample vials. At this point, rejected sample vials 14' may be diverted by a rejecting mechanism (here, a pivoting gate) 50 to a rejects conveyor 52, and accepted sample vials 14" may be allowed to continue on to the next stage of the line. It is readily understood by those skilled in the art that, in addition to a pivoting gage, rejecting mechanisms 50 may be used in conjunction with the present invention 10 to separate or otherwise identify accepted sample vials 14" and rejected sample vials 14'.

Figure 4:
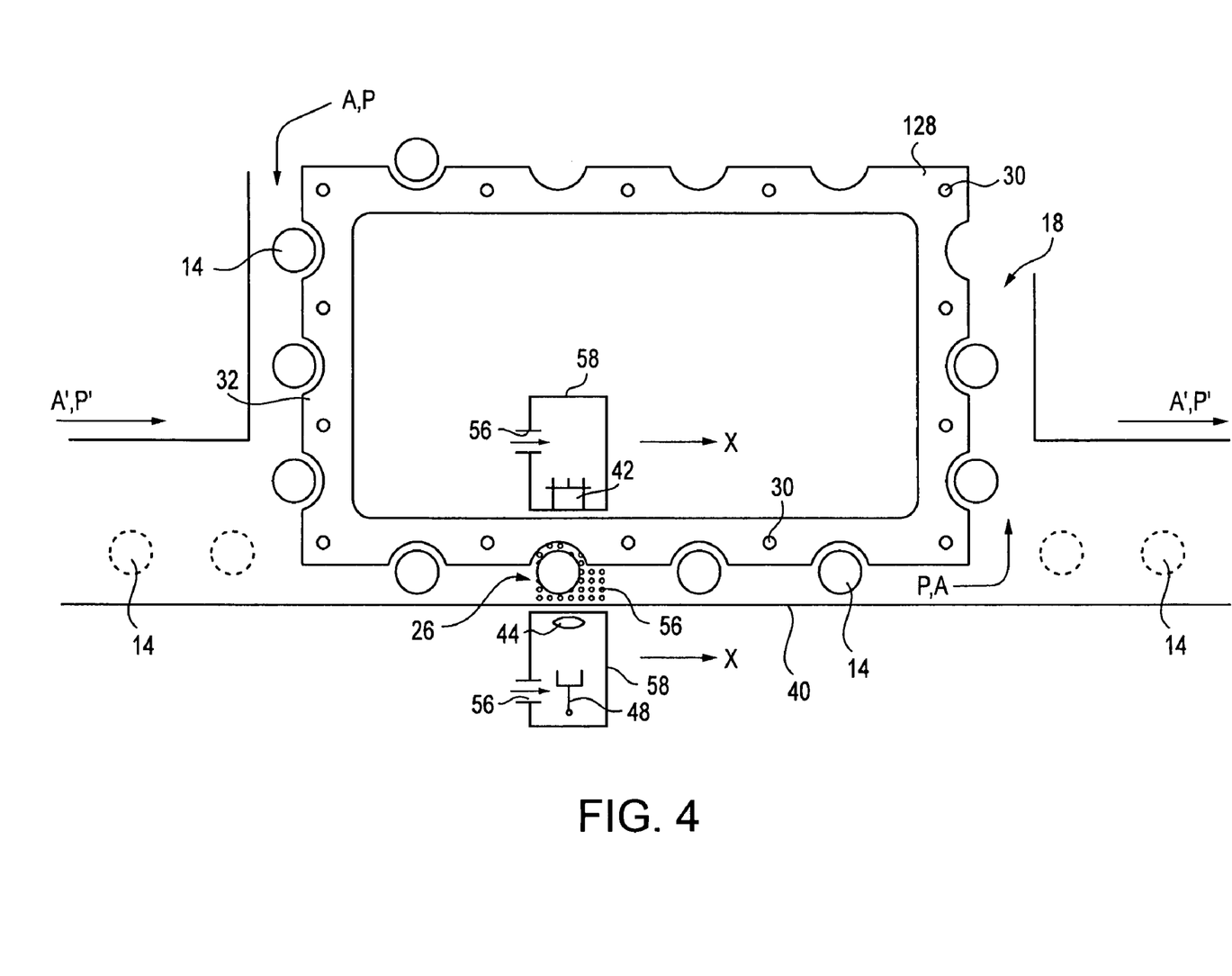
FIG. 4 is a schematic plan view of an inspection region according to a second embodiment of the invention.

FIG. 4 shows an inspection region 18 according to a second embodiment of the present invention. Reference characters identifying the elements in FIG. 4 that are the same as those used in FIGS. 1–3B, identify substantially the same elements, and the description thereof is eliminated herein. Rather than a starwheel 28, the embodiment shown in FIG. 4 uses a linear feeder 128 to convey the sample vials 14 to the sensing area 26. The vial accommodation portion 32 of she second embodiment is not round, but is rectangular in shape, and may be made of a pliable material (e.g., rubber or silicone) or may be made of a series of interconnected links. The vial accommodation portion rotates in the direction A to move the sample vials 14 and reference vial(s) in the path of movement P. In FIG. 4, the sample vials 14 can be introduced from the pre-inspection region (not shown in FIG. 4) to the linear feeder 128 from above the linear feeder (when viewing FIG. 4, i.e., from a direction substantially orthogonal to the path of movement P of the vials 14, 30 when the vials are passing through the sensing area 26), or can be introduced to the linear feeder in a direction substantially parallel to the path of movement P of the vials 14, 30 when the vials are passing through the sensing area, in the direction A' along the path of movement P', as these sample vials 14 are shown in hatched lines. Alternatively, the sample vials can be fed to the linear feeder 128 in a direction oblique to the path of movement P of the vials 14, 30. Similarly, after the vials 14, 30 are inspected, the sample vials 14 can be introduced to the post-inspection region 20 (not shown in FIG. 4) from virtually any direction along the linear feeder 128, e.g. along direction A' in path of movement P' (the sample vials 14 of which are shown in hatched lines), or along direction A in path of movement P.

It is noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for nondestructive automated headspace analysis comprising:
   A) a container conveyor comprising:
      a pre-inspection region, an inspection region and a post-inspection region;
      a plurality of first housings configured to house a respective plurality of generally optically transparent sealed test containers each configured to contain a gas to be measured; and
      at least one second housing configured to house a respective at least one sealed reference container containing a reference gas,
      said container conveyor configured to:
         1) convey, along a movement path, said plurality of first housings such that a respective of the plurality of generally optically transparent sealed test containers are conveyed through said pre-inspection region, said inspection region and said post-inspection region; and
         2) convey, along the movement path, said at least one second housing such that a respective at least one sealed reference container is conveyed through said inspection region; and
   B) a sensor located in said inspection region and comprising:
      1) a laser source configured to emit a laser beam for absorption in the gas to be measured and the reference gas, said laser source further configured to emit the laser beam such that the laser beam intersects with the movement path;
      2) a beam detector configured to detect the laser beam; and
      3) a zone configured to accept the plurality of test containers and the at least one reference container conveyed by said container conveyor, said zone located between said detector and said laser source;
   wherein said container conveyor is further configured to alternatingly convey at least one first housing of said plurality of first housings and said at least one second housing such that a respective at least one sealed test container of the plurality of sealed test containers and the at least one sealed reference container are alternatingly conveyed through said zone.

2. The system according to claim 1, wherein the at least one sealed reference container comprises a plurality of sealed reference containers, and wherein said at least one second housing comprises a plurality of second housings, such that said container conveyor is configured to convey, along the movement path, the plurality of sealed reference containers.

3. The system according to claim 2, wherein:
   1) the plurality of sealed reference containers comprises:
      a) a first plurality of sealed reference containers corresponding to a first range of reference gas characteristics; and
      b) a second plurality of sealed reference containers corresponding to a second range of reference gas characteristics;

2) said laser source comprises:
   a) a first laser source configured to emit a first laser beam that intersects a movement path of the first plurality of sealed reference containers; and
   b) a second laser source configured to emit a second laser beam that intersects a movement path of the second plurality of sealed reference containers; and
3) said detector comprises:
   a) a first detector configured to detect the first laser beam; and
   b) a second detector configured to detect the second laser beam.

4. The system according to claim 3, further comprising a processor configured to check, using the first and second pluralities of sealed reference containers, the calibration of the detector respectively over the first range of reference gas characteristics, and over the second range of reference gas characteristics.

5. The system according to claim 4, wherein the first and second characteristics are pressure and concentration.

6. The system according to claim 3, wherein the reference gas is a respective first and second different reference gas, such that said laser source emits the laser beam for absorption in respective first and second different reference gases.

7. The system according to claim 2, wherein each sealed reference container of the plurality of reference containers contains a reference gas within a range of reference gas characteristics, such that said laser source emits the laser beam for absorption in the reference gas within a range of reference gas characteristics.

8. The system according to claim 7, further comprising a processor configured to check the calibration of the detector over the range using the plurality of reference containers.

9. The system according to claim 2, wherein:
   said container conveyor comprises a rotatable starwheel located at the inspection region, said starwheel comprising a portion of said plurality of first housings and configured to:
      accept, in said portion of said plurality of first housings, the plurality of sealed test containers from said pre-inspection region;
      convey said at least one first housing and said at least one second housing such that a respective of the at least one sealed test container and the at least one sealed reference container are conveyed through said zone; and
      convey, via said portion of said plurality of first housings, the plurality of sealed test containers to said post inspection region;
   the plurality of sealed reference containers is held in said corresponding plurality of second housings, said corresponding plurality of second housings being affixed to said starwheel; and
   said zone is located at a portion of said starwheel.

10. The system according to claim 9, wherein said starwheel is configured to convey, via said at least one first housing, the at least one sealed test container through said zone at a slower rate than when said starwheel is not passing the at least one sealed test container through said zone.

11. The system according to claim 2, wherein said container conveyor is configured to convey, via said at least one first housing, the at least one sealed test container through said zone at a slower rate than when said container conveyor is not passing the at least one sealed test container through said zone.

12. The system according to claim 2, further comprising a purging system configured to purge ambient surroundings of the zone of the gas to be measured.

13. The system according to claim 9, wherein said starwheel is configured such that a single first housing of said portion of said plurality of first housings holds a single sealed test container of the plurality of sealed test containers between a pair of sealed reference containers of the plurality of sealed reference containers.

14. The system according to claim 13, wherein said starwheel is configured such that a single second housing of said plurality of second housings holds a single sealed reference container of the pair of sealed reference containers between a pair of sealed test containers of the plurality of sealed test containers.

15. The system according to claim 2, wherein:
   said container conveyor comprises a linear feeder located at the inspection region, said linear feeder comprising a portion of said first plurality of housings and configured to:
      accept, in said portion of said plurality of first housings, the plurality of sealed test containers from said pre-inspection region;
      convey said at least one first housing and said at least one second housing such that a respective of the at least one sealed test container and the at least one sealed reference container are conveyed through said zone; and
      convey, via said portion of said plurality of first housings, the plurality of sealed test containers to said post inspection region;
   the plurality of sealed reference containers is held in said corresponding plurality of second housings, said corresponding plurality of second housings being affixed to said linear feeder; and
   said zone is located at a portion of said linear feeder.

16. The system according to claim 15, wherein said linear feeder is configured to convey, via said at least one first housing, the at least one sealed test container through said zone at a slower rate than when said linear feeder is not passing the at least one sealed test container through said zone.

17. The system according to claim 2, wherein said laser source and said beam detector are configured to move in a direction substantially parallel to the movement path of the at least one sealed test container when the at least one sealed test container is conveyed through said zone.

18. A method for automated nondestructive headspace analysis comprising:
   conveying, along a movement path, a plurality of generally optically transparent sealed test containers each configured to contain a gas to be measured, through a pre-inspection region, an inspection region and a post-inspection region of a container conveyor;
   alternatingly conveying, along the movement path, the plurality of test containers, and at least one sealed reference container, through a zone of an inspection region of the container conveyor;
   transmitting a laser beam in the zone of the inspection region, in a direction that intersects the movement path, and through a single sealed test container of the plurality of test containers, when the single sealed test container is conveyed through the zone;
   transmitting the laser beam in the zone of the inspection region, in the direction that intersects the movement path, and through a single at least one sealed reference container, when the single sealed reference container is conveyed through the zone;

detecting, using a detector, the transmitted laser beam; and conveying, along the movement path, the plurality of test containers through a post-inspection region of a container conveyor.

19. The method according to claim 18, wherein the at least one sealed reference container comprises a plurality of sealed reference containers.

20. The method according to claim 19, wherein:
the plurality of sealed reference containers comprises:
  a) a first plurality of sealed reference containers corresponding to a first range of reference gas characteristics; and
  b) a second plurality of sealed reference containers corresponding to a second range of reference gas characteristics; and
said transmitting the laser beam in the zone of the inspection region, in the direction that intersects the movement path, and through a single at least one sealed reference container, when the single sealed reference container is conveyed through the zone, comprises:
  a) transmitting a first laser beam in the zone of the inspection region, and through a single sealed reference container of the first plurality of reference containers; and
  b) transmitting a second laser beam in the zone of the inspection region, and through a single sealed reference container of the second plurality of reference containers.

21. The method according to claim 20, further comprising checking, using the first and second pluralities of sealed reference containers, the calibration of the detector respectively over the first range and over the second range.

22. The method according to claim 21, wherein the first and second characteristics are pressure and concentration.

23. The method according to claim 20, wherein the reference gas is a respective first and second different reference gas.

24. The method according to claim 19, wherein each sealed reference container of the plurality of reference containers contains a reference gas within a range of reference gas characteristics.

25. The method according to claim 24, further comprising checking the calibration of the detector over the range, using the plurality of sealed reference containers.

26. The method according to claim 24, wherein:
said alternately conveying comprises:
  accepting, using a starwheel, the plurality of sealed test containers from the pre-inspection region;
  conveying, using the starwheel, the at least one sealed test container and the at least one sealed reference container through the zone; and
  conveying the plurality of sealed test containers to the post inspection region;
the plurality of sealed reference containers are affixed to the starwheel; and
the zone is located at a portion of the starwheel.

27. The method according to claim 26, wherein said conveying, using the starwheel, the at least one sealed test container and the at least one sealed reference container through the zone comprises conveying the at least one sealed test container through the zone at a slower rate than when the starwheel is not passing the at least one sealed test container through the zone.

28. The method according to claim 26, further comprising arranging, on the starwheel, a single sealed test container of the plurality of sealed test containers between a pair of sealed reference containers of the plurality of sealed reference containers.

29. The method according to claim 28, further comprising arranging, on the starwheel, a single sealed reference container of the pair of sealed reference containers between a pair of sealed test containers of the plurality of sealed test containers.

30. The method according to claim 24, wherein said alternately conveying comprises conveying the at least one sealed test container through the zone at a slower rate than when the at least one sealed test container is not conveyed through the zone.

31. The method according to claim 24, further comprising purging ambient surroundings of the zone of the gas to be measured.

32. The method according to claim 19, wherein:
said alternately conveying comprises:
  accepting, using a linear conveyor, the plurality of sealed test containers from the pre-inspection region;
  conveying, using the linear conveyor, the at least one sealed test container and the at least one sealed reference container through the zone; and
  conveying the plurality of sealed test containers to the post inspection region;
the plurality of sealed reference container being affixed to the linear conveyor; and
the zone being located at a portion of the linear conveyor.

33. The method according to claim 19, wherein said conveying, using the linear conveyor, the at least one sealed test container and the at least one sealed reference container through the zone comprises conveying the at least one sealed test container through the zone at a slower rate than when the linear conveyor is not passing the at least one sealed test container through the zone.

34. The method according to claim 19, further comprising moving the laser beam and the beam detector in a direction substantially parallel to the movement path of the at least one sealed test container when the at least one sealed test container is conveyed through the zone.

35. The method according to claim 18, wherein the alternately conveying comprises:
accepting the plurality of sealed test containers from the pre-inspection region,
successively conveying the plurality of test containers and a plurality of the reference containers through the zone, such that the laser beam successively passes through the plurality of test containers and the plurality of reference containers, and
conveying the plurality of sealed test containers to the post inspection region.

36. The method according to claim 18, wherein the alternately conveying comprises:
accepting the plurality of sealed test containers from the pre-inspection region,
successively conveying the plurality of test containers and a single one of the at least one reference container through the zone, such that the laser beam successively passes through the plurality of test containers and the single reference container, and
conveying the plurality of sealed test containers to the post inspection region.

37. The method according to claim 18, wherein the alternately conveying comprises:

accepting the plurality of sealed test containers from the pre-inspection region, successively conveying a single one of the plurality of test containers and a plurality of the reference containers through the zone, such that the laser beam successively passes through the single test container and the plurality of reference containers, and conveying the plurality of sealed test containers to the post inspection region.

38. The method according to claim 18, wherein the alternately conveying comprises:

accepting the plurality of sealed test containers from the pre-inspection region, successively conveying a single one of the plurality of test containers and a single one of the plurality of the reference containers through the zone, such that the laser beam successively passes through the single test container and the single reference container, and conveying the plurality of sealed test containers to the post inspection region.

* * * * *